US011529222B2

(12) United States Patent
Auer

(10) Patent No.: US 11,529,222 B2
(45) Date of Patent: Dec. 20, 2022

(54) DEVICE FOR ARTIFICIALLY INSEMINATING A MAMMAL

(71) Applicant: SMARTBOW GMBH, Weibern (AT)

(72) Inventor: Wolfgang Auer, Weibern (AT)

(73) Assignee: SMARTBOW GMBH, Weibern (AT)

( * ) Notice: Subject to any disclaimer, the term of this patent is extended or adjusted under 35 U.S.C. 154(b) by 354 days.

(21) Appl. No.: 16/383,736

(22) Filed: Apr. 15, 2019

(65) Prior Publication Data

US 2019/0231502 A1 Aug. 1, 2019

Related U.S. Application Data

(63) Continuation of application No. PCT/AT2017/000072, filed on Oct. 18, 2017.

(30) Foreign Application Priority Data

Oct. 18, 2016 (AT) .................................. A 480/2016

(51) Int. Cl.
*A61D 19/02* (2006.01)
*A61B 17/43* (2006.01)

(52) U.S. Cl.
CPC ......... *A61D 19/027* (2013.01); *A61D 19/025* (2013.01); *A61B 17/43* (2013.01)

(58) Field of Classification Search
CPC ..... A61B 17/43; A61D 19/025; A61D 19/027
See application file for complete search history.

(56) References Cited

U.S. PATENT DOCUMENTS

| 2,942,603 | A | | 6/1960 | Geyer | |
|---|---|---|---|---|---|
| 3,811,443 | A | * | 5/1974 | Dickinson, III | ..... A61D 17/002 600/35 |
| 6,676,596 | B2 | | 1/2004 | Erwin et al. | |
| 8,390,681 | B1 | * | 3/2013 | Burkman | ............... G16H 10/40 348/79 |

(Continued)

FOREIGN PATENT DOCUMENTS

| CN | 2197019 | 5/1995 |
|---|---|---|
| CN | 2197019 Y | 5/1995 |

(Continued)

OTHER PUBLICATIONS

PCT International Preliminary Report on Patentability and Written Opinion, International Filing Date Oct. 18, 2017, International Application No. PCT/AT2017/000072, Date of issuance of report Apr. 23, 2019.

(Continued)

*Primary Examiner* — Christine H Matthews
(74) *Attorney, Agent, or Firm* — Scott C. Mayhew

(57) ABSTRACT

A device for artificially inseminating a mammal with sperm from a male breeding animal is disclosed, the sperm being introduced through the vagina of the animal into or onto the uterus of the animal which is to be inseminated. The device comprises a tube which can be moved on the uterus through the vagina of the animal which is to be inseminated, and a heatable chamber for accommodating a thin tube containing the sperm, and a drive for removing the sperm from the thin tube and the uterus-sided opening of the tube. The device comprises a mechanism enabling the thin tube to be moved out from the chamber into the tube.

10 Claims, 2 Drawing Sheets

(56) References Cited

U.S. PATENT DOCUMENTS

| | | | |
|---|---|---|---|
| 10,687,928 B2* | 6/2020 | Biscay | ............... A61B 1/00066 |
| 2002/0151764 A1 | 10/2002 | Erwin et al. | |
| 2006/0217590 A1 | 9/2006 | Tack | |
| 2011/0282135 A1* | 11/2011 | Waybright | ........... A61D 19/027 600/35 |
| 2013/0129331 A1 | 5/2013 | de Souza et al. | |

FOREIGN PATENT DOCUMENTS

| | | | | |
|---|---|---|---|---|
| CN | 1172634 | A | | 2/1998 |
| CN | 1307480 | A | | 8/2001 |
| CN | 1351484 | A | | 5/2002 |
| CN | 101262951 | | | 9/2008 |
| CN | 102002515 | | | 4/2011 |
| CN | 102002515 | A | | 4/2011 |
| CN | 202288531 | | | 7/2012 |
| CN | 103717166 | A | | 4/2014 |
| CN | 103942303 | A | | 7/2014 |
| CN | 203841849 | U | | 9/2014 |
| CN | 203841849 | U | * 9/2014 | ............... A61D 7/00 |
| CN | 104127954 | | | 11/2014 |
| CN | 104546219 | | | 4/2015 |
| CN | 205163311 | U | | 4/2016 |
| CN | 105994005 | | | 10/2016 |
| DE | 60030361 | | | 10/2006 |
| DE | 60030361 | T2 | | 9/2007 |
| EP | 2215992 | A1 | | 8/2010 |
| EP | 3528745 | | | 7/2020 |
| FR | 1472139 | A | | 3/1967 |
| JP | 2001-017026 | | | 1/2001 |
| KR | 20150004453 | A | | 1/2015 |
| SU | 1831330 | | | 7/1993 |

OTHER PUBLICATIONS

PCT Notification of Transmittal of Translation of the International Preliminary Report on Patentability, International Filing Date Oct. 18, 2017, International Application No. PCT/AT2017/000072, dated May 2, 2019.

Mexican Patent Office Action, Non-English, dated Jun. 24, 2022, Mexican Patent Application No. MX/a/2019/004618 filed Oct. 18, 2017.

Mexican Patent Office Action, English Translation, dated Jun. 24, 2022, Mexican Patent Application No. MX/a/2019/004618 filed Oct. 18, 2017.

CCPIT, Chinese Patent Office Action with Search Report, Non-English, dated May 22, 2020, Chinese Patent Application No. 201780064366.7, filed Oct. 18, 2017.

CCPIT, Chinese Patent Office Action with Search Report, English Translation, dated May 22, 2020, Chinese Patent Application No. 201780064366.7, filed Oct. 18, 2017.

Chilean Patent Office Action with Search Report, Non-English, Chilean Patent Application No. 201901036, dated Apr. 16, 2019.

Russian Patent Office Action with Search Report, Non-English and English Translation, dated Feb. 17, 2021, Russian Patent Application No. 2019111506(022449), filed Oct. 18, 2017.

Japanese Patent Office Action with Search, English Translation, dated Jul. 30, 2021, Japanese Patent Application No. 2019-541825, filed Apr. 12, 2019.

* cited by examiner

DEVICE FOR ARTIFICIALLY INSEMINATING A MAMMAL

CROSS REFERENCE TO RELATED APPLICATIONS

This application is a continuation of PCT International Application No. PCT/AT2017/000072, filed Oct. 18, 2017, which claims the benefit of Austrian Patent Application No. A 480/2016, filed Oct. 18, 2016, both of which are expressly incorporated herein by reference in their entirety.

TECHNICAL FIELD

The invention relates to a device for artificially inseminating a mammal, such as, typically, a cow.

BACKGROUND

In the artificial insemination of a cow, sperm of a bull is introduced into the uterus of the fertile cow using an instrument in order, as intended, to effect fertilization of an ovum of a cow there and thus to produce a young animal. The main reason for choosing artificial insemination instead of natural copulation is that it is easier to select an optimal sire, which may also live far away, for the given breeding purpose.

At present, artificial insemination of a cow is typically done as follows:

Beforehand, depending on the desired breeding goal, a decision has been made about which bull the sperm to be used should come from. The sperm, which is diluted with special substances for transport in the frozen state, is stored in a so-called thin tube for transport and handling, the thin tube typically being configured as a straw-like, narrow, double-sided tube sealed on both ends. The capacity of a thin tube is typically 0.25 to 0.5 ml. In typical bull-to-cow transport, several thin tubes are surrounded by liquid nitrogen—i.e., chilled to −196° C.—in a heat-insulating container. For artificial insemination, an inseminator removes the appropriate thin tube from the heat-insulating container containing liquid nitrogen, and typically heats the thin tube approximately to body temperature in water at 37° C. for about 30 seconds. By thawing the sperm contained in the thin tube, the semen become active again. In the next step, the thin tube is inserted into the insemination syringe (often called "insemination gun"). The insemination syringe is essentially a slender tube within which a thin rod can be moved longitudinally as a piston. For inserting the thin tube into the insemination syringe, the piston at the face of the insemination syringe is pushed out a bit, then one end of the thin tube is pushed onto the piston, then the piston together with the thin tube is pulled back into the tube so that the thin tube disappears into the tube. If, after the insertion of the small tube into the insemination syringe by the inseminator, a certain distance to the cow must be covered, the insemination syringe is typically maintained at body temperature by the inseminator holding it against his/her body, under his/her clothes. In the next step, the insemination syringe is inserted face first into a so-called insemination sheath, which is essentially a sterile plastic tubing for one-time use, until the face of the insemination syringe abuts from the inside against the front of the insemination sheath, which is closed except for a small opening.

Then, the insemination syringe, which is surrounded by the insemination sheath, is inserted face first into the vagina of the cow. This procedure requires great skill on the part of the inseminator. While holding and moving the insemination syringe with one hand, his/her second hand is in the rectum of the cow, in order to feel the position of the insemination syringe with the fingertips through the wall of the rectum and vagina, and to feel the cow's cervix and keep it still so that the face of the insemination syringe can be pushed into and through the cervix. Ideally, when the insemination syringe extends approximately 0.6 to 1.25 cm into the uterus, the insemination syringe is triggered. Triggering moves the plunger into the rear end of the thin tube, forcing the contents of the thin tube out of the front end and pushing it through the fine opening on the face of the insemination sheath into the uterus of the cow.

There are several approaches to simplify individual steps of this workflow and/or to reduce their error rate:

US 2013129331 A1 describes a portable device among other things for heating the thin tubes carrying the bull's sperm. In essence, the device consists of a container for water and an electric heating device for it, which is battery operated and temperature regulated.

U.S. Pat. No. 6,676,596 B2 shows a lightweight, portable, temperature-regulated heated housing for receiving, preheating and keeping warm an insemination syringe loaded with a preheated thin tube during transport to the place of use.

KR 20150004453 A shows a device for the regulated heating and keeping warm of a loaded or empty insemination syringe. As intended, the insemination syringe is inserted into the inner tube of the device, configured as a double-walled tube. In the space between the two tubes the device comprises a regulated electric heating device, which can be connected via a plug with a socket of a vehicle and thereby can be supplied with electric energy.

DE 60030361 T2 describes a device which, as intended, can be used optionally either as an insemination syringe or for the transplantation of a fertilized ovum into the uterus of a farm animal.

The device comprises a long, narrow tube and a thin tubing which can be moved therein and beyond at the face end. Optionally, a thin tube is connected to the rear end of the tubing and a drive means is connected at the end of the thin tube facing away from the tubing. As intended, the thin tube is inserted into the vagina up to the uterus of the animal, then the tubing is moved further into the uterus, then sperm is pushed out of the thin tube and through the entire tubing into the uterus of the animal. The part comprising the thin tube is formed as a tube made of a heat-retaining material, the purpose of which is to keep the temperature constant at the otherwise preheated thin tube and also to mechanically protect the thin tube and the adjoining parts of the device. The problem with this device is that the sperm which is to be introduced into the uterus must flow through a relatively long tubing after leaving the thin tube. This makes it difficult to avoid a large amount of sperm ultimately remaining in the tube. In addition, the tubing can either be used only for a single insemination procedure, or it must be very laboriously cleaned and sterilized after an insemination procedure.

U.S. Pat. No. 2,942,603 A shows an insemination syringe, which has the shape of a gun and serves for the artificial insemination of poultry. Liquid sperm is introduced into a tubular, electrically heatable chamber of the insemination syringe. By manually pressing a trigger lever, a piston is pushed from one end into the chamber, whereby the liquid sperm is pushed out of the chamber and a tube connected therewith.

The disadvantage is that sperm remains as a contamination in the chamber. Thus, the syringe must be cleaned laboriously before it can be used again, because otherwise it is unclear which sperm has finally triggered a fertilization.

BRIEF SUMMARY

It is the object of the invention to design a device for artificially inseminating a mammal such as typically a cow, so that, with ease of handling, the certainty is increased that the sperm which is to be introduced into the uterus of the animal during introduction is not mixed with other sperm present in the insemination device.

The problem is solved by assuming a construction in which the device for artificial insemination comprises a heatable chamber, which can be heated and in which a sperm-containing thin tube can be stored and heated and/or maintained at a temperature. As an improvement according to the invention, it is proposed to equip the device with a mechanism by means of which the thin tube can be removed from the chamber into an elongated tube which is introduced into the animal which is to be inseminated.

Since the thin tube can be heated in said chamber of the device for the artificial insemination, the intermediate step of heating a thin tube prior to the in any case necessary introduction into the device can be omitted.

Since the thin tube can be advanced through part of the device into said elongated tube which is intended to be inserted into the animal being inseminated, the sperm contained in the small tube need not come into contact with the wall of the tube. Thus, the tube can be used more often even without intermediate cleaning, and sperm from different sires can be used in consecutive insemination procedures without the risk of mixing or unclear assignment.

By regulating the heating, temperature-time profiles including optimal final temperature at the thin tube can be specified exactly in a tight range and reliably maintained by the regulation, reliably preventing temperature shocks to the sperm.

The regulated heating is best established by means of one or more ohmic electric heating resistors, one or more temperature sensors, a preferably rechargeable electric battery, and a control unit including actuators for the electric current through the electric heating resistor(s). The further technical details can be defined in the context of professional actions, so that it need not be further discussed here.

BRIEF DESCRIPTION OF THE DRAWINGS

The invention will be illustrated by means of highly stylized drawings of exemplary devices according to the invention for the artificial insemination.

DETAILED DESCRIPTION OF THE DISCLOSURE

Figure 1:
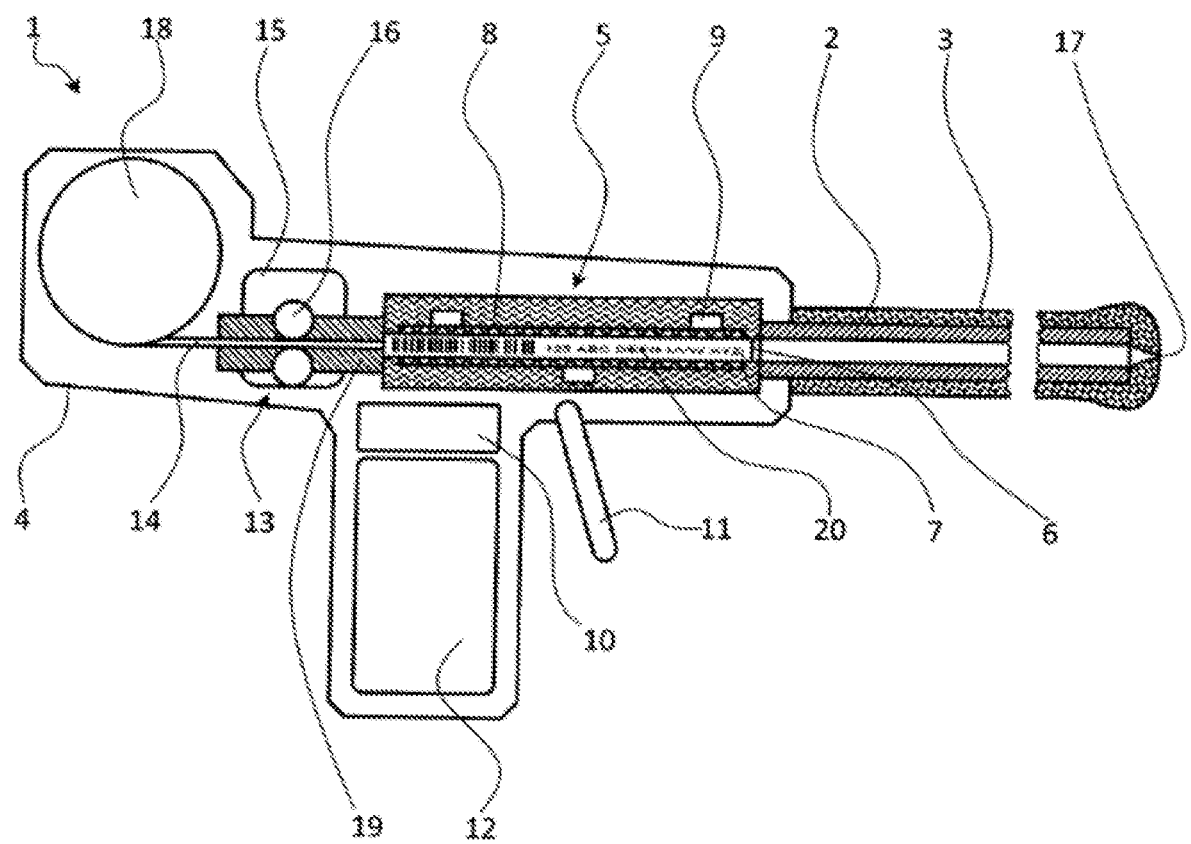
FIG. 1: is a partial lateral sectional view of a first, simple embodiment of an exemplary device according to the invention.

The front part of the device 1 according to the invention of FIG. 1 which, as intended, is to be inserted with its distal end first into the vagina of the animal, is on the right side in FIG. 1. It has a similar structure to classic insemination syringes. It comprises a long, slender tube 2 which is open at both faces and which is covered by a single-use insemination sheath 3 before insertion into the vagina.

The rear proximal end of tube 2 is rigidly connected to a housing 4 and protrudes into said housing. In housing 4 is an elongated heating unit 5 which is coaxially aligned with tube 2. Heating unit 5 comprises a chamber 6 which is continuous in the longitudinal direction of said heating unit. In the operational state of device 1 shown in FIG. 1, the thin tube 7 containing the sperm which ultimately is to be introduced into the uterus of the animal is arranged in chamber 6.

The lateral surface of small tube 7 is closely embraced by the lateral surface of elongated chamber 6 in heating unit 5, and thus held in a tightly defined position. Preferably, as directly as possible on the lateral surface of chamber 6 and thus at the contact area of heating unit 5 with thin tube 7, heating unit 5 is equipped with an electric heating resistor 8. When electric current flows through heating resistor 8, said heating resistor heats up and gives off heat to its surroundings and thus to thin tube 7. In the vicinity of heating resistor 8 and thin tube 7, temperature sensors 9 are arranged, which deliver an electric signal to a controller 10 in response to the temperature prevailing at them. In controller 10, a target heating curve for the temperature profile over time is stored at temperature sensors 9 for the heating procedure of a thin tube 7. Once the heating procedure is triggered, which can be done by pressing trigger lever 11, the controller sends electric current through heating resistor 8 fittingly, so as to heat it such that said temperature profile is achieved at temperature sensors 9 in the best way possible, whereby thin tube 7 is heated in an optimal way. The required electric energy is provided by an electric battery 12, which ideally is rechargeable. (Instead of a heat source based on the principle of ohmic resistance in which electric energy is converted into heat, a microwave or induction-based principle for converting electric energy into heat could also be used.)

When the thin tube has reached the target temperature for the artificial insemination, this temperature is regulated by the control loop formed by the elements heating resistor 8, temperature sensors 9 and controller 10 to stably maintain this value. Now, at any time, drive 13 can be started by pressing trigger lever 11 again, which ultimately urges the sperm contained in thin tube 7 into the uterus of the animal which is to be inseminated.

In the advantageous exemplary embodiment sketched in FIG. 1, drive 13 comprises a piston 14, which is configured as an elastically flexible wire, an electric motor 15 and a pair of drive rollers 16.

The front part of piston 14 is aligned coaxially with thin tube 7 on its rear face. As with insemination syringes according to the prior art also, the diameter of piston 14 is dimensioned such that it fits in the rear face of thin tube 7 which is formed as a small tube, and upon movement towards thin tube 7 abuts in it at a closure plug.

When drive 13 is in service, electric motor 15 drives rotation of drive rollers 16 which with their lateral surface abut against the lateral surface of the piston and which are rotatably mounted on housing 4, such that they displace piston 14 in its longitudinal direction in the direction of thin tube 7. As soon as the face of piston 14 abuts against the thin tube, the piston removes thin tube 7 from heating unit 5 into tube 2 which is coaxially positioned with respect to chamber 6 of heating unit 5, which, at this time, with its distal longitudinal region facing away from housing 4, already protrudes at the optimal depth for the artificial insemination procedure into the vagina or uterus of the animal which is to be inseminated. By piston 14, thin tube 7 is also displaced in tube 2 to its front (=distal) end until thin tube 7 abuts against the distal face of insemination sheath 3 which stops its movement. By further movement of piston 14 towards thin tube 7, the previously mentioned closure plug in thin tube 7 is displaced in the direction of its front end—i. e. into the thin tube—whereby, by the pressure built-up of the sperm contained in small tube 7, a valve is opened and the sperm first exits thin tube 7 and then passes through a small opening 17 on the face in insemination sheath 3 and thus, as intended, finds its way into the uterus of the animal which is to be inseminated. If thin tubes are used which do not comprise such a valve but have to be cut off at the front end, such cutting off can be done manually prior to attaching the small tube in heating device 5, or device 1 is equipped with an automatic cutting device which cuts off the thin tube. This cutting device may be formed, for example, by a small cutting edge which can pivot in a narrow angular range, and upon which one or two electromagnets act to drive a pivoting movement. Ideally, this cutting device is mounted between heater 5 and tube 2.

After this operation, device 1 is moved away from the animal so that tube 2 and insemination sheath 3 finally come completely out of the animal's vagina. Drive 13 is switched to the opposite direction, so that piston 14 is retracted again and most of its longitudinal region is wound onto roller 18. Ideally, for this purpose, roller 18 can also be driven by an electric motor to rotate. Finally, thin tube 7 comes to a stop at piston guide part 19 in the vicinity of the rear face of heating unit 5. By further movement of piston 14, said piston is withdrawn from thin tube 7 and the empty thin tube 7 remains alone in chamber 6 of the heating unit.

For example, for the introduction and removal of thin tube 7 into or out of heating unit 5, the heating unit may be displaceable in its longitudinal direction out of housing 4 in a manner such that the openings on the face of chamber 6 become accessible. The displaceability of heating unit 5 relative to housing 4 can be achieved, for example, by arranging said heating unit in a channel and holding it displaceably while being arranged in the channel longitudinal direction, wherein the channel extends laterally through the device. It is also possible to arrange a plurality of heating units in the direction of the channel next to each other and to connect them to an assembly and thus make them displaceable together through the duct, wherein only said heating unit touches contacts with power supply for the heating which is in the position where its chamber 6 is in the line of movement of piston 14. Said assembly which holds a plurality of heating units can be imagined, for example, as the cylinder of a revolver, wherein a heating unit is arranged in the individual chambers in each case instead of a cartridge.

Instead of moving and emptying thin tube 7 with the aid of a piston 14, it could also be moved by fluid pressure, preferably gas pressure, out of chamber 6 and into tube 2, and also be emptied. For this purpose, the gas pressure would have to be built up from the side of chamber 6 facing away from tube 2 by a pump or other pressure source such as a CO2 cartridge, and for this purpose thin tube 7 must abut sealingly tight with its lateral surface in chamber 6 or in tube 2 against the inner lateral surface of chamber 6 or the tube.

For the next artificial insemination procedure, only the used parts insemination sheath 3 and thin tube 7 need to be replaced by new parts on device 1.

In a preferred embodiment, after its emptying procedure, thin tube 7 is not moved back through tube 2 into chamber 6, but rather remains at the distal end of tube 2 and is removed from there via the distal opening of tube 2 during or after removal of insemination sheath 3. This further avoids the risk of the inner lateral surface of tube 2 coming into contact with sperm from thin tube 7.

According to an advantageous development, a reading device, typically a small camera, which reads identification information 20 provided on thin tube 7, is mounted in heating unit 5. The information can be stored by controller 10 together with further information for documentation purposes for immediate or later read-out. Identification information 20 can be attached, for example, as a label in form of a barcode and/or an alphanumeric character string on the outer lateral surface of thin tube 7.

Figure 2:
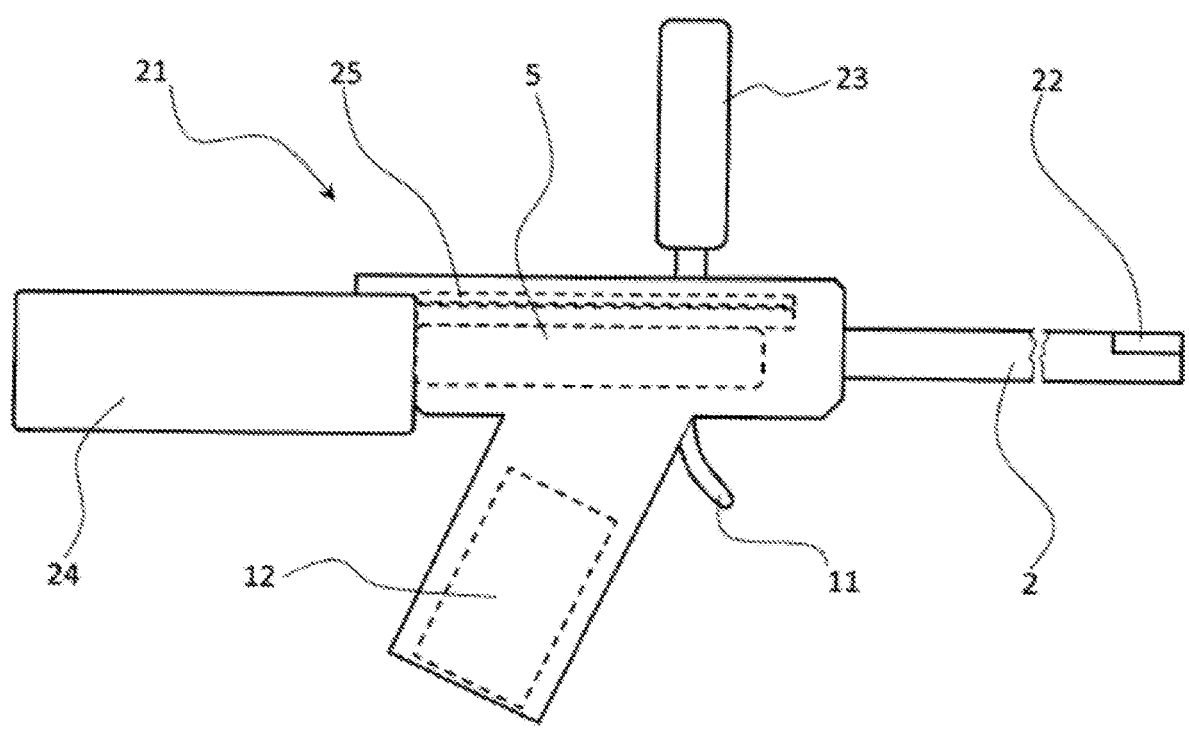
FIG. 2: shows a side view of a second device according to the invention, which offers several additional functions over that of FIG. 1. Some of the hidden fixtures are represented by dashed lines.

Since the device for artificial insemination according to the invention already contains an electronic controller and an electric energy storage unit, advantageous developments include the accommodation of further functional assemblies, which can perform useful functions using electronic or electromechanical components, on the device. FIG. 2 illustrates such functions.

Exemplary device 21 for artificially inseminating a mammal according to the invention shows parts the function of which has already been explained with reference to FIG. 1. These parts are tube 2, heating unit 5, trigger lever 11 and battery 12. The other functional parts shown in FIG. 2 are:

An optical acquisition unit, sensor unit 22, is mounted at the front (distal) end of tube 2. This can be an endoscope camera 22, which is also equipped with a light source. The image information captured by this camera during insertion of the tube can be displayed on display 23. This makes it easier to move tube 2 in the respective correct direction and to recognize when tube 2 is inserted far enough. Furthermore, it also makes it possible to make unnecessary without the aforementioned feeling of the position of the tube from the intestine, which of course represents a tremendous simplification of work for the inseminator.

Under certain circumstances, information can also be identified as to whether the animal is even fertile.

As an alternative or in addition to endoscope camera 22—which operates in the spectral range of visible light—sensor unit 22 can also be or contain NIR sensor technology. That is, it contains one or more light sources—typically laser diodes—for one or more near infrared light spectra, as well as incident light sensors from the near infrared spectral range. As is known per se, it is thus possible to detect concentrations of various substances such as hemoglobin, leucocytes, or water in the observed surface tissue based on the intensity of specific individual spectral ranges in relation to certain other spectral ranges. Based on the concentrations of hemoglobin and water, for example, an indication can be provided as to whether the animal may actually be in heat.

Measurement results and automatically drawn conclusions therefrom can be displayed on display 23, and a drop-down menu for choosing further steps can also be offered. For example, the option can be offered to discontinue an insemination procedure if it has been found by NIR spectroscopy that the animal appears not to be in heat at all, or if based on a high concentration of leukocytes detected it must be assumed that the animal has inflammation.

Of course, information about the respective status of parts of device 21 can also be displayed on display 23, as well as information about the particular thin tube currently contained.

On the housing of device 21, a cooling container 24 may be releasably attachable, which may include a movable depot in which there are several thin tubes, wherein an individually selected thin tube can be brought by electromechanical components of device 21 to a removal system and transported into heating unit 5. Depending on whether frozen sperm or sperm merely held at low temperature is to be transported in the small tubes, cooling tank 24 can be configured for carrying along liquid nitrogen, or merely for maintaining a cooling temperature that is not especially high.

Device 21 includes an optical sensor 25 cooperating with a light source, by means of which the sperm is transilluminated and optically analyzed for the density of live sperm cells.

Devices 1, 21 according to the invention can be equipped with electronic parts for so-called body-coupled communication (BCC for short). These parts are, in particular, sensors which detect the contact of the device by the inseminator and/or the contact of the device with the animal which is to be inseminated and then communicate electronically with a device carried by the inseminator or attached to the animal, wherein the body of the inseminator or the animal is used as an electric conductor for the transmission of electric signals. Thus it can be automatically recorded and documented which inseminator has treated which animal with which insemination device 1, 21.

The following data can be stored, for example: personal data of the inseminator, animal identification, data regarding the animal which provided the sperm, and the date, time and place at which the insemination took place. (The latter information may typically be determined by a suitably equipped animal ear tag on the animal and transmitted by BCC to the device for insemination.)

By automatically capturing identification information about the animal which is to be inseminated and the sperm used, it is also possible to automatically check, by networking device 1, 21 in a wireless network, whether the correct thin tube is actually being used for the correct animal. In the positive case, the insemination procedure can be automatically approved, while in the negative case, the insemination procedure can be automatically blocked.

The information about the identity of the respective thin tube does not necessarily have to be available and to be read out optically. It is also possible, for example, to equip the thin tubes or cooling containers 24 containing them with RFID chips, from which information is read out by a reading mechanism on device 1, 21.

On rod 2 which is to be inserted, further sensors can be mounted, by means of which information can automatically be obtained as to whether the animal is actually fertile or not. The evaluation of this information can be done automatically, completely or partially in the control part of the device. In the negative case, the insemination can be stopped in time, so as not to consume the respective thin tube. The information to be obtained by such sensors may concern, for example, the temperature in the vagina or uterus of the animal, or a pH, or the presence of certain hormones, or color information on tissue or fluid surrounding the sensor.

An ultrasonic sensor can provide information about the nature of the surrounding tissue and also about the position of the sensor itself.

The invention claimed is:

1. A device for artificially inseminating a female animal with sperm from a male breeding animal, the device configured to introduce sperm through a vagina of the female animal into or onto a uterus of the female animal which is to be inseminated, said device comprising a tube which can be moved to the uterus through the vagina of the female animal which is to be inseminated, and a heatable chamber for accommodating a thin tube containing sperm and opening towards a proximal end of the tube, and a drive configured to remove sperm from the thin tube and from a uterus-sided opening of the tube, wherein the drive is further configured to move the thin tube from the heatable chamber into the tube, the drive having a piston movable from a side facing away from the tube into the heatable chamber and through the heatable chamber into the tube, said device further comprising an optical sensor configured to analyze a density of living sperm cells in the thin tube, and wherein the piston is formed by an elastically flexible wire, wherein a portion of the wire is wound on a roller.

2. The device according to claim 1, wherein the chamber is part of a heating unit which can be moved relative to a housing of the device.

3. The device according to claim 2, wherein the heating unit can be moved perpendicular to the axis of the tube.

4. The device according to claim 3, further comprising a reading device capable of reading identification information from the thin tube.

5. The device according to claim 1, further comprising an endoscope camera mounted at a distal region of the tube.

6. The device according to claim 1, further comprising an NIR sensor mounted at a distal region of the tube.

7. The device according to claim 1, further comprising a display, which is controlled by a controller of the device, and that the controller is configured to show status information regarding at least one of the device, information regarding a state of the animal, and status information regarding a current insemination procedure on the display.

8. The device according to claim 1, further comprising a detachably connectable cooling container configured for receiving a plurality of small tubes.

9. The device according to claim 1, wherein the device is equipped for electronic communication by a sensor configured to detect contact of the device with the female animal.

10. The device according to claim 1, wherein sensors are mounted on the tube for a measurement of state variables in the vagina or on the uterus of the female animal which is to be inseminated and a controller contained in the device is configured to evaluate measurement results automatically as to whether the female animal is fertile or not and then to approve or abort an insemination procedure.

* * * * *